United States Patent
Kupferschmid et al.

(10) Patent No.: US 7,422,590 B2
(45) Date of Patent: Sep. 9, 2008

(54) SURGICAL INSTRUMENT

(75) Inventors: Bernhard Kupferschmid, Emmingen-Liptingen (DE); Rupert Mayenberger, Rielasingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 813 days.

(21) Appl. No.: 10/848,543

(22) Filed: May 18, 2004

(65) Prior Publication Data
US 2004/0260338 A1 Dec. 23, 2004

(30) Foreign Application Priority Data
Jun. 20, 2003 (DE) ................. 103 28 512

(51) Int. Cl.
*A61B 18/18* (2006.01)
(52) U.S. Cl. ................. 606/51; 606/45; 606/46
(58) Field of Classification Search .......... 606/45, 606/46, 48–52
See application file for complete search history.

(56) References Cited

U.S. PATENT DOCUMENTS

| 5,151,102 A | * | 9/1992 | Kamiyama et al. ............ 606/51 |
| 5,352,222 A | * | 10/1994 | Rydell ...................... 606/37 |
| 5,484,436 A | * | 1/1996 | Eggers et al. ................ 606/48 |
| 5,540,685 A | * | 7/1996 | Parins et al. ................. 606/51 |
| 5,658,281 A | * | 8/1997 | Heard ........................ 606/48 |
| 5,766,166 A | * | 6/1998 | Hooven ...................... 606/45 |
| 5,779,701 A |   | 7/1998 | McBrayer et al. |
| 5,860,975 A | * | 1/1999 | Goble et al. .................. 606/45 |
| 5,893,846 A | * | 4/1999 | Bales et al. .................. 606/32 |
| 5,908,420 A | * | 6/1999 | Parins et al. ................. 606/51 |
| 6,193,718 B1 |   | 2/2001 | Kortenbach et al. |
| 6,334,860 B1 |   | 1/2002 | Dorn |
| 2002/0019632 A1 |   | 2/2002 | Mayenberger |

FOREIGN PATENT DOCUMENTS

| DE | 297 13 631 | 11/1997 |
| DE | 198 58 512 | 5/2000 |
| DE | 198 55 812 | 6/2000 |
| DE | 100 23 534 | 11/2001 |
| EP | 0 572 131 | 12/1993 |
| EP | 1 153 578 | 11/2001 |
| WO | 96/22740 | 8/1996 |
| WO | 03/013376 | 2/2003 |

\* cited by examiner

*Primary Examiner*—Michael Peffley
(74) *Attorney, Agent, or Firm*—Lipsitz & McAllister, LLC

(57) ABSTRACT

In order to improve a surgical instrument having at least one tool comprising a carrier and at least one functional component adhesively bonded to the carrier, in such a way that the carrier can be easily and securely adhesively bonded to the functional component, whilst maintaining the desired function of the instrument, it is proposed that the carrier comprise a first contact surface, that the functional component comprise a second contact surface, and that the first contact surface bear on the second contact surface without any gap therebetween.

27 Claims, 4 Drawing Sheets

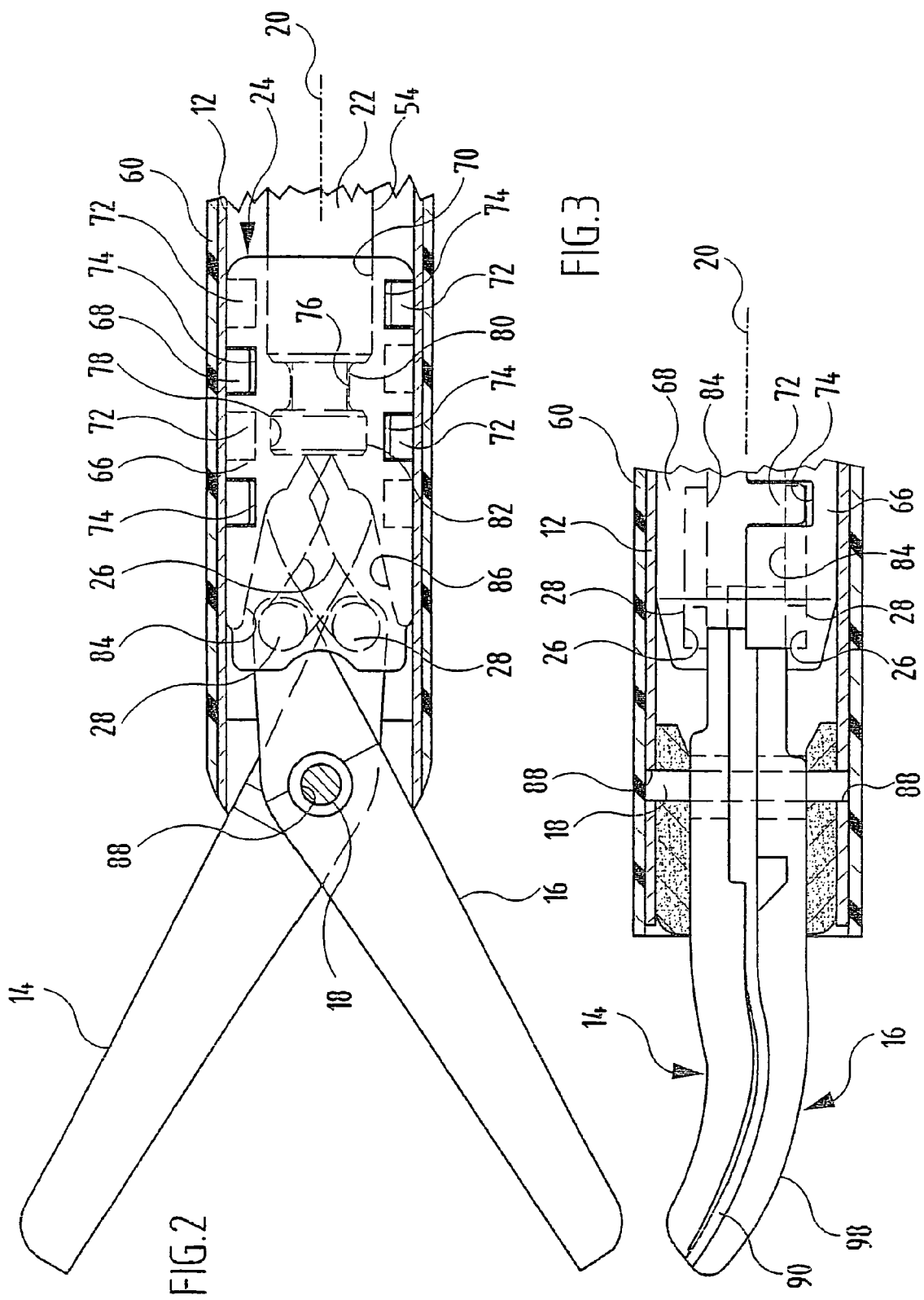

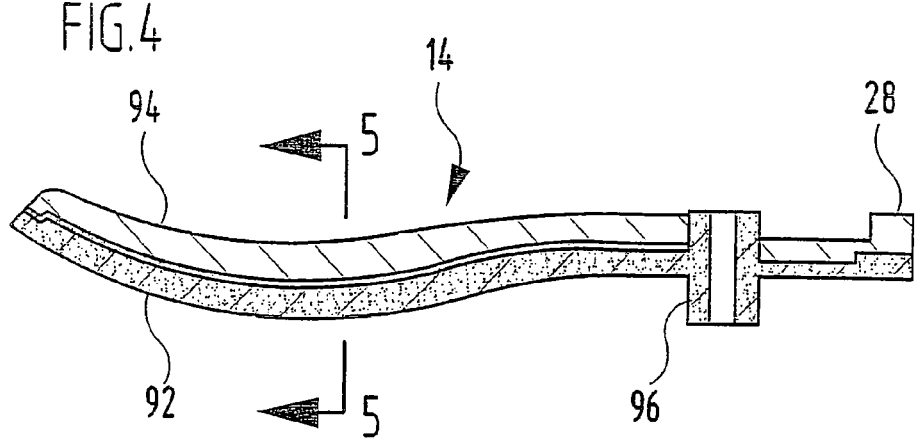
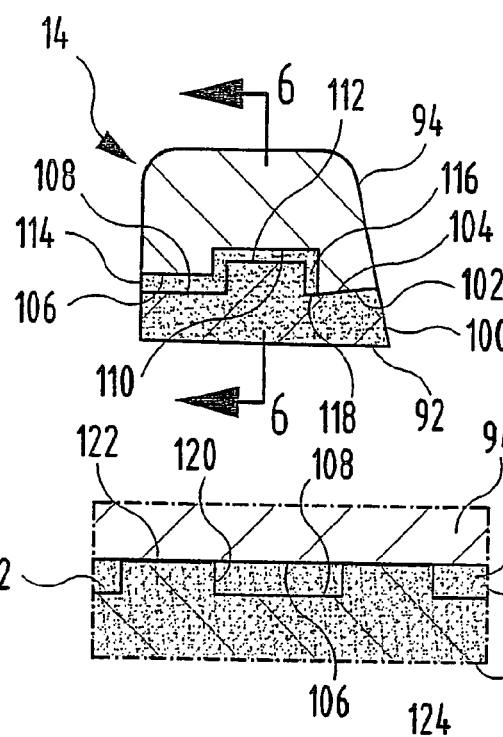
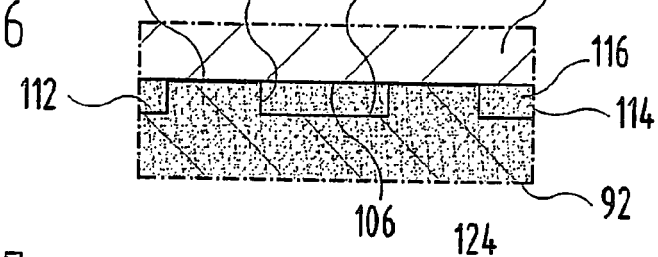
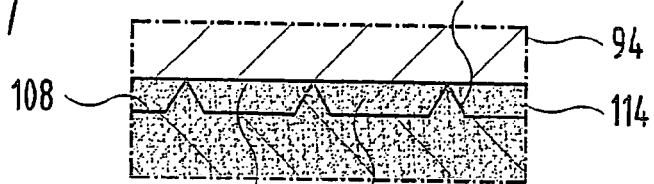
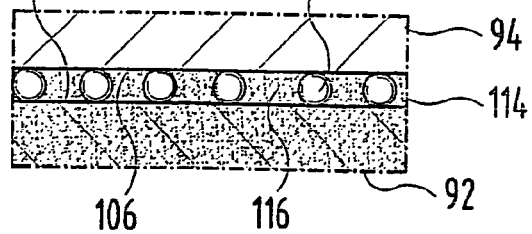

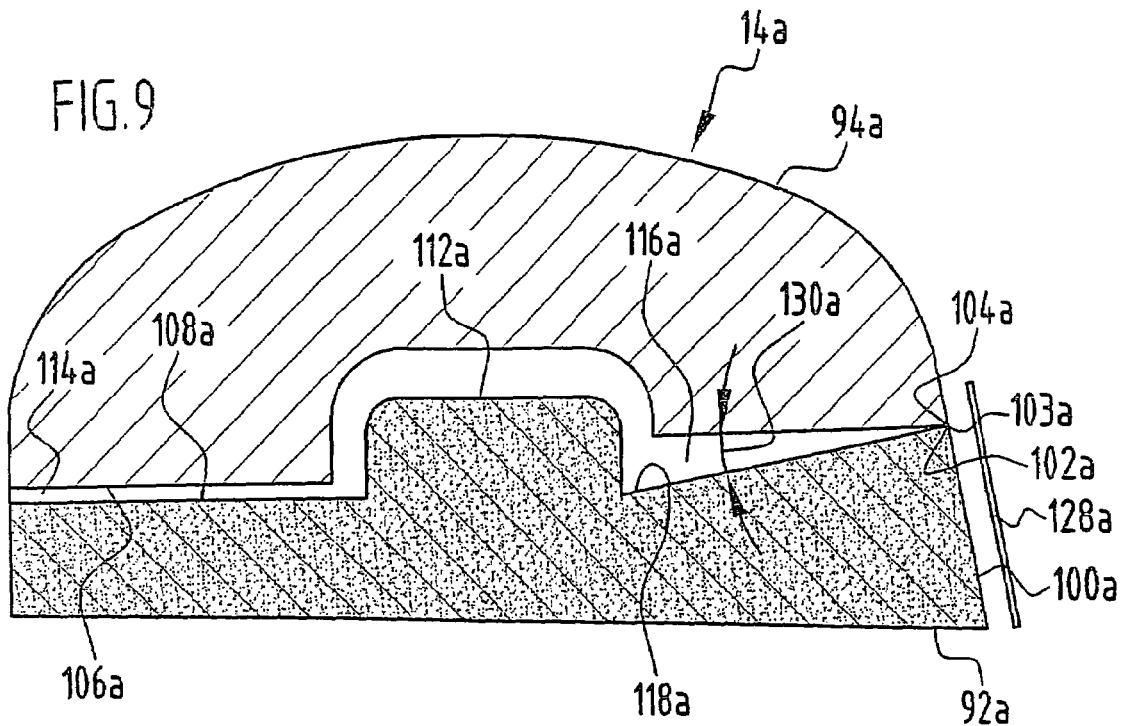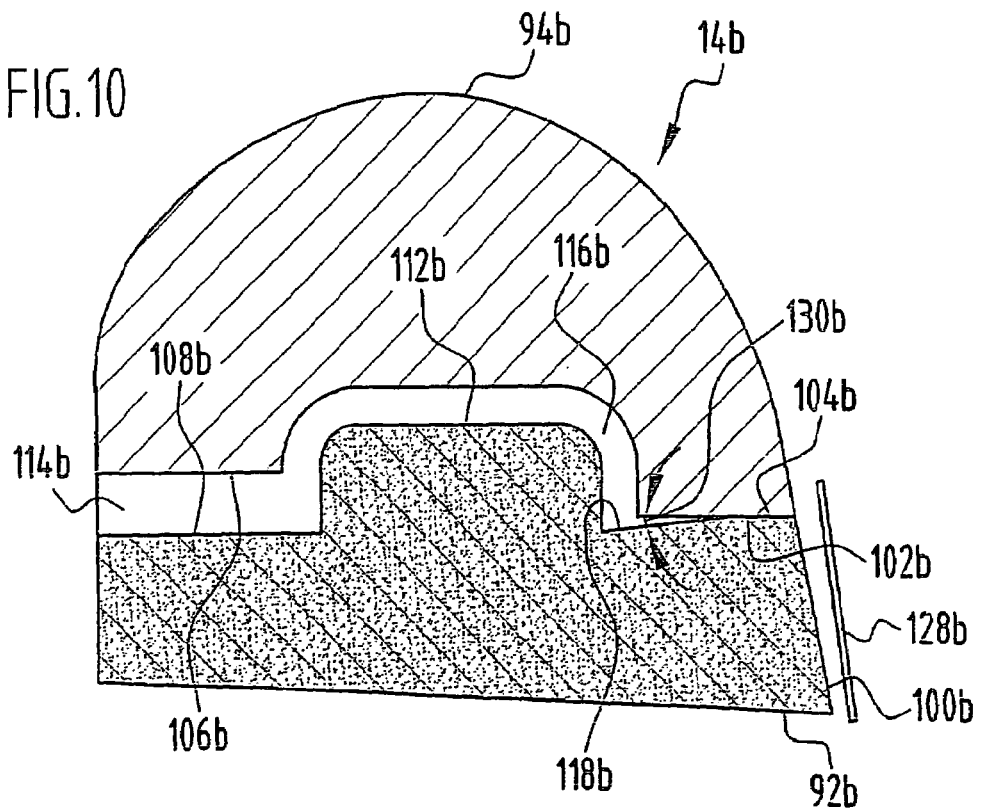

SURGICAL INSTRUMENT

The present disclosure relates to the subject matter disclosed in German application No. 103 28 512.1 of Jun. 20, 2003, which is incorporated herein by reference in its entirety and for all purposes.

BACKGROUND OF THE INVENTION

The present invention relates to a surgical instrument with at least one tool comprising a carrier and at least one functional component adhesively bonded to the carrier.

Surgical instruments of the kind described at the outset are known, for example, in the form of scissors comprising a metallic or plastic scissor blade to which a ceramic or metal cutter is adhesively bonded. Such a two-part construction of the tool is used, for example, in bipolar instruments, as such instruments require tools which are electrically insulated from one another. When current is passed over the tool during use of the instrument, this may cause evaporation of the adhesive along the cutting edge.

The object of the present invention is, therefore, to so improve a surgical instrument of the kind described at the outset that the carrier can be easily and securely adhesively bonded to the functional component, whilst maintaining the desired function of the instrument.

SUMMARY OF THE INVENTION

This object is accomplished with a surgical instrument of the kind described at the outset, in accordance with the invention, in that the carrier comprises a first contact surface, in that the functional component comprises a second contact surface, and in that the first contact surface bears on the second contact surface without any gap therebetween.

With carrier and functional component designed accordingly, such a construction has the advantage that a defined coagulation path is formed along the area of transition between the carrier and the functional component, for example, between a metal and a ceramic material, when the instrument is used as bipolar instrument. Furthermore, when current is passed along the contact surfaces, evaporation of an adhesive cannot occur because adhesive cannot get in between the contact surfaces in this area during the bonding owing to the two contact surfaces bearing on each other without any gap between them.

It is expedient for the first contact surface to bear directly and/or without any adhesive on the second contact surface. It is thus impossible for the adhesive to evaporate when current is passed over the tool.

It is conceivable for the instrument to be designed in a multiplicity of ways for different purposes. It could, for example, be designed as forceps, fixation forceps or needle holder, with the at least one tool being constructed accordingly. It is, however, advantageous for the at least one tool to be a scissor blade comprising a cutter, for the cutter to comprise a cutting edge, and for the first and second contact surfaces in the area of the cutting edge to bear directly on each other or continue into the cutting edge. Owing to the functional component bearing on the carrier without any gap therebetween, a precisely defined cutting edge which can be of particularly smooth design without any undesired projections is formed. In particular, no bonding agent, for example, in the form of an adhesive or any other bonding material, such as, for example, soldering tin, can leak in the area of transition between the carrier and the functional component and thereby alter the shape of the area of transition in an undesired manner.

The first contact surface and the second contact surface preferably bear on each other along at least one contacting line with no gap therebetween. Adhesive introduced between the two contact surfaces in order to join these, is, for example, thereby prevented from forming part of the surface of the tool, in particular, in the area of the cutting edge. In particular, this would have the disadvantage that, if a coagulation current flowed along this surface of the tool, the adhesive could evaporate in an undesired manner and be released in the human body. In addition, damage could be caused to the instrument.

It is particularly expedient for the first contact surface and the second contact surface to bear surface-to-surface on each other at least section-wise in the area of a common contacting surface with no gap therebetween. In particular, when the two contact surfaces are adhesively bonded to each other, a particularly reliable adhesive-free separation between the two contact surfaces is thereby ensured. Even when particularly large coagulation currents flow along the surface of the tool, evaporation of the adhesive is thereby prevented.

In accordance with a preferred embodiment of the invention, provision may be made for the carrier to comprise a first adhesive surface, for the functional component to comprise a second adhesive surface, for the first adhesive surface to be separated from the second adhesive surface by an adhesive gap, and for the adhesive gap to be filled with an adhesive layer which is substantially formed by an adhesive. This configuration ensures that the functional component can be bonded in a desired manner to the carrier. The formation of the adhesive gap enables introduction of the adhesive in a defined manner between the two adhesive surfaces of the carrier and the functional component.

It is particularly advantageous for the adhesive gap to be of wedge-shaped construction at least section-wise. In this way, manufacturing tolerances of carrier and functional component are particularly easy to compensate. Furthermore, the two parts can thereby be made to bear on each other along a contacting line.

It is expedient for a thickness of the wedge-shaped adhesive gap to decrease in the direction towards the first and second contact surfaces bearing on each other. By virtue of such a construction of the adhesive gap, on the one hand, a secure connection between carrier and functional component is ensured, and, on the other hand, an amount of adhesive between the two parts and adjacent to the contact surfaces bearing on each other without a gap therebetween or adjacent to the contacting line is minimized.

In accordance with a preferred embodiment of the invention, provision may be made for the first contact surface to define at least section-wise a first plane, for the second contact surface to define at least section-wise a second plane, and for the first plane and the second plane to be inclined at an angle of inclination relative to each other and intersect in a contacting line of the first and second contact surfaces. In this way, for example, a wedge-shaped adhesive gap with the above-described advantages can be formed.

In order to make the at least one tool as compact as possible, it may be expedient for the angle of inclination to be less than 45°, preferably less than 20°. In particular, with very small angles of inclination in the range of less than 20°, only a minimal amount of adhesive is required for bonding the carrier and the functional component reliably and permanently to each other.

At least one spacer is preferably arranged in the adhesive gap between the first and second adhesive surfaces. The at least one spacer ensures that the functional component cannot tilt relative to the carrier. This could happen because the carrier and the functional component bear with their two contact surfaces on each other without a gap therebetween, whereas a gap can be formed in the remaining area of the surfaces of the carrier and the functional component that are to be bonded to each other. The at least one spacer thus defines a minimum spacing between the first and second adhesive surfaces, so that the first contact surface and the second contact surface can bear with their entire surface on each other.

The construction of the instrument becomes particularly simple when the first and/or the second adhesive surface carry the at least one spacer. Thus, for bonding purposes, adhesive can either be injected into the adhesive gap or applied to one or both of the adhesive surfaces before the carrier is brought into contact with the functional component. A desired spacing is automatically maintained between the functional component and the carrier by the at least one spacer.

Alternatively or additionally, it is conceivable for the adhesive to contain the at least one spacer. Such a configuration has the advantage that both the carrier and the functional component can be manufactured in a particularly simple way, and, in accordance with manufacturing tolerances actually determined after the manufacture of the two parts, spacers having the necessary size can be selected and added to the adhesive, or that an adhesive with corresponding spacers can be directly selected.

It is expedient for a plurality of spacers to be provided. This results in a plurality of contact points between the functional component, the spacer and the carrier, so that the adhesive gap is formed in a desired manner.

In principle, a multiplicity of shapes are conceivable for the at least one spacer. It is particularly advantageous for the at least one spacer to be of spherical, pyramidal, conical, cylindrical or parallelepipedal shape. Such shapes can be manufactured in a particularly simple and defined manner.

In principle, the adhesive surfaces of the carrier and the functional component could be of completely smooth design. In accordance with a preferred embodiment of the invention, provision is, however, made for the surface of at least one adhesive surface to have at least one structured surface portion. Formation of a structure on the adhesive surfaces results in enlargement of these, which contributes towards increasing the adhesive strength between the carrier and the functional component.

It is expedient for the structured surface portion to essentially comprise a symmetrical structure. Such a configuration is particularly easy to produce. For example, pyramids with different shapes or interlockings could be selected. The structured surface portion can simultaneously serve as spacer.

Alternatively or additionally, it is also conceivable for the structured surface portion to be microstructured. This could, for example, be accomplished by glass bead matting. In addition, a microstructured surface has the advantage that adhesive molecules can be bonded particularly well to the carrier and/or the functional component.

To increase the adhesive strength it is advantageous for the surface of the first and/or the second adhesive surface to be larger than a projection of the first and/or the second adhesive surface onto the respective other adhesive surface. Such a configuration ensures that the adhesive surface, as a whole, is enlarged, which increases a surface of application for the adhesive.

In principle, it is conceivable to bond identical materials to one another. When the instrument is to be used for electrosurgical procedures, it is advantageous for the carrier to be electrically conductive and for the functional component to be electrically non-conductive. In this case, the functional component serves as insulator. A reverse construction of the tool is also conceivable.

For the construction of scissors, it is expedient for the first tool to be movable, in particular, mounted for pivotal movement, relative to a second tool.

In order for the instrument to also be usable for endoscopic surgical procedures, provision may be made, in accordance with a preferred embodiment of the invention, for the instrument to be a tubular shaft instrument with an elongated shaft, and for the at least one tool to be movably mounted at the distal end of the shaft.

It is expedient for the instrument to be scissors. This enables the instrument to be used as, for example, bipolar scissors.

The following description of preferred embodiments of the invention serves in conjunction with the drawings to explain the invention in greater detail.

BRIEF DESCRIPTION OF THE DRAWINGS

FIG. 2 is an enlarged view of detail A in FIG. 1;

FIG. 3 is a longitudinal sectional view, turned through 90° in relation to the view in FIG. 2, of scissors with closed scissor blades;

FIG. 4 is an enlarged view of a scissor blade;

FIG. 5 is a sectional view along line 5-5 in FIG. 4;

FIG. 6 is a sectional view along line 6-6 in FIG. 5;

FIG. 7 shows a second embodiment of a scissor blade according to the invention in a view similar to FIG. 6;

FIG. 8 shows a third embodiment of a scissor blade in a view similar to FIG. 6;

FIG. 9 shows a fourth embodiment of a scissor blade in a view similar to FIG. 5; and FIG. 10 shows a fifth embodiment of a scissor blade in a view similar to FIG. 5.

DETAILED DESCRIPTION OF THE INVENTION

Figure 1:
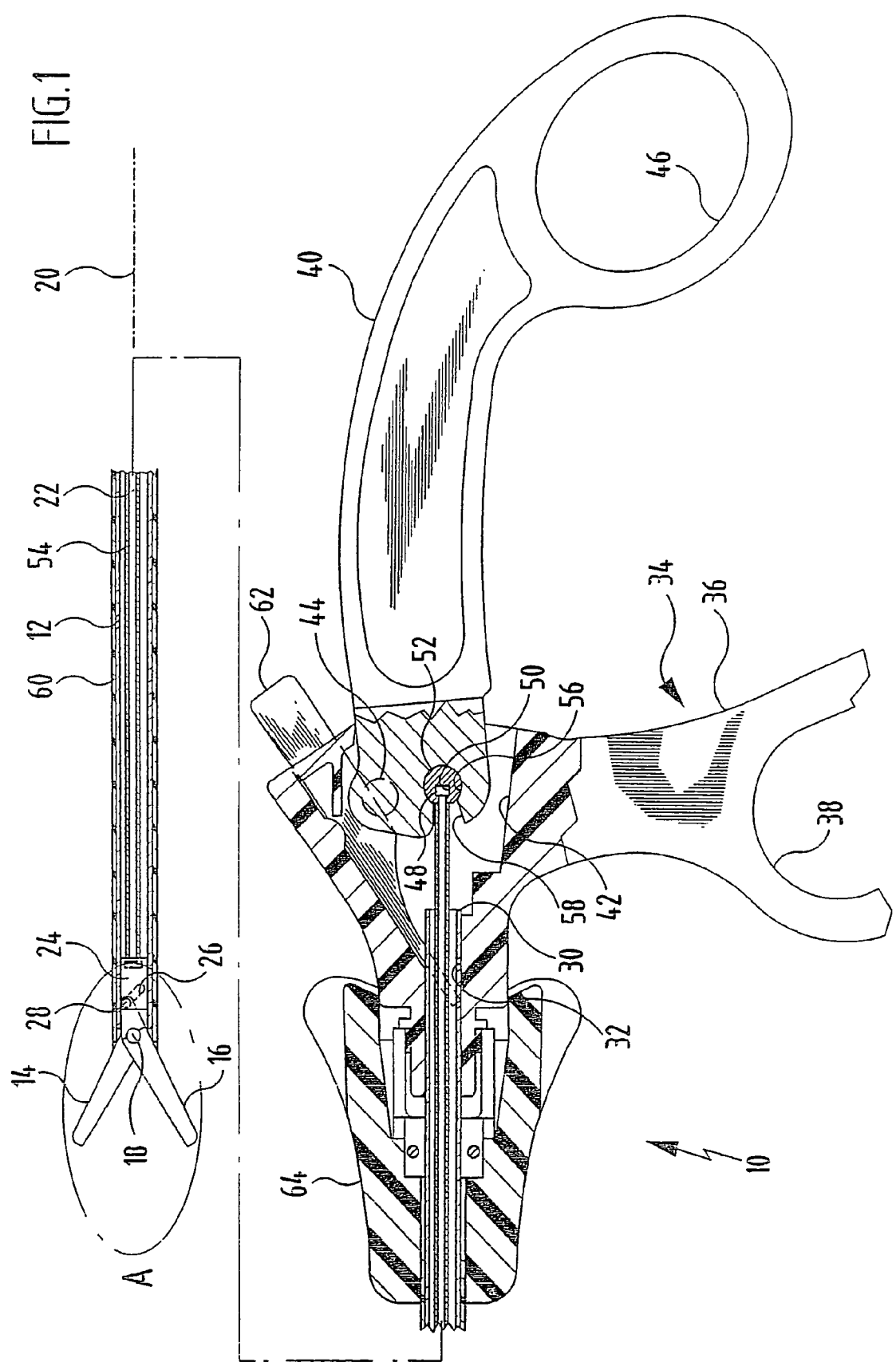
FIG. 1 is a longitudinal sectional view of scissors according to the invention.

A longitudinal sectional view of bipolar scissors generally designated by the reference numeral 10, constructed as an endoscopic tubular shaft instrument, is shown in FIG. 1.

The bipolar scissors 10 comprise an elongated, tubular shaft 12, at the distal end of which two scissor blades 14 and 16 pivotable relative to each other are mounted on a bearing pin 18 which extends through the shaft 12 on either side thereof and transversely to a longitudinal axis 20 of the shaft 12.

For moving the scissor blades 14 and 16 a drive member 24 is arranged at a distal end of a push-and-pull rod 22 which is longitudinally displaceable in the direction of the longitudinal axis 20 in the shaft 12. The drive member 24 is provided with two guide slots 26 in which bearing pins 28 projecting from the scissor blades 14 and 16 transversely to the longitudinal axis 20 engage and are guided as a result of an axial displacement of the drive member 24, whereby the scissor blades 14 and 16 are opened and closed, respectively.

At its proximal end 30, the shaft 12 is accommodated in a longitudinal bore 32 of a stationary handle part 34, from which a stationary branch 36 with a finger opening 38 extends essentially transversely to the longitudinal axis 20 away from the latter. On the handle part 34, a second branch 40 is mounted in a recess 42 open in proximal direction for pivotal movement about a bearing bolt 44 extending through the recess 42 transversely to the longitudinal axis 20 and comprises at its free end a further finger opening 46.

A proximal end of the push-and-pull rod 22 is provided with a short cylindrical head 48 which engages in a positively locking manner in a bearing groove 50, expanding with a single step, of a bearing cylinder 52 and is held therein. The push-and-pull rod 22, which is covered with an electrical insulating layer 54, projects from the bearing groove 50. A longitudinal axis of the bearing cylinder 52 extends transversely to the longitudinal axis 20. The bearing cylinder 52 is held on the branch 40 in the proximity of the bearing bolt 44 in a bearing bore 56, which extends transversely to the longitudinal axis 20 and has a slot 58 expanding in distal direction from the center of the bearing bore 56.

As well as the push-and-pull rod 22, the shaft 12 is surrounded by an electrically insulating layer 60. Both the shaft 12 and the push-and-pull rod 22 are connected in a manner not shown in detail to a bipolar connection 62, by means of which the bipolar scissors 10 can be connected by means of lines to an electrical energy supply unit. Via both the push-and-pull rod 22 and the shaft 12, an electric connection is established to one of the two scissor blades 14 and 16, respectively, which are insulated relative to each other. This makes it possible, for example, in order to coagulate tissue, to pass a high-frequency current over the scissor blades 14 and 16 and to sever the coagulated tissue following the coagulation procedure.

Also provided is a rotary knob 64 which is non-rotatable relative to the shaft 12, but is rotatable relative to the handle part, so that the distal end of the bipolar scissors 10 with the two scissor blades 14 and 16 can be rotated relative to the two branches 36 and 40 about the longitudinal axis 20.

FIG. 2 shows an enlargement of detail A in FIG. 1. The drive body 24, which is made up of two half shells 66 and 68, serves to move the two scissor blades 14 and 16. The two half shells 66 and 68 are of identical construction and are essentially in the form of half a cylinder severed in longitudinal direction. For assembly, the two half shells 66 and 68 each have two pairs of connecting pins 72 projecting in circumferential direction and two pairs of recesses 74 accommodating these. The recesses 74 and the connecting pins 72 are alternately formed along the edge of the half shells 66 and 68 extending parallel to the longitudinal axis 20. In the assembled state, i.e., in a coupled position, in which the two half shells 66 and 68 are joined to each other and connect the push-and-pull rod 22 to the two scissor blades 14 and 16, the two half shells 66 and 68 form at the proximal side a rod receptacle 70 in the form of a bore. This tapers with a single step on a short section and then expands again in diameter with a single step, so that a ring projection 76 is formed between the rod receptacle 70 and a ring groove 78.

A distal end of the push-and-pull rod 22 has a ring groove 80 which corresponds with the ring projection 76, and adjoining the ring groove 80 a cylindrical head 82 designed so as to correspond with the ring groove 78.

At the distal side the two half shells 66 and 68 are provided with essentially V-shaped recesses 84 and 86 open in distal direction. One of the two guide slots 26 is machined in the direction of the shaft 12 in each recess. The two guide slots 26 form a groove which is open transversely to and towards the longitudinal axis 20, and in which the bearing pins 28 of the scissor blades 14 and 16 each engage transversely to the longitudinal axis 20 and so as to point away from the longitudinal axis 20. The guide slots 26 are slightly curved.

To assemble the front end of the bipolar scissors 10, the two scissor blades 14 and 16 are first inserted with their bearing pins 28 into the respective guide slots 26 and the push-and-pull rod 22 is placed with its head 82 in the ring groove 78.

The half shells 66 and 68 are pushed together transversely to the longitudinal axis 20 so that each connecting pin 72 of the half shell 66 engages a recess 74 of the half shell 68 and vice versa. The half shells 66 and 68 are not adhesively bonded to each other or undetachably joined to each other in any other way.

Following the above-described assembly of the parts, the push-and-pull rod 22 is inserted from the distal end into the shaft 12 until the shaft 12 surrounds the half shells 66 and 68. Once the half shells 66 and 68 are inserted in the shaft 12, the push-and-pull rod 22 and the scissor blades 14 and 16 are undetachably joined to each other in axial direction as the shaft 12 secures the half shells 66 and 68 against release from the push-and-pull rod 22. Finally, the bearing pin 18 is pushed through bores 88 extending transversely to the longitudinal axis in the shaft 12, whereby the scissor blades 14 and 16 are fixed on the shaft 12 and owing to movement of the push-and-pull rod in axial direction and guidance of the bearing pins 28 in the guide slots 26, only a pivotal movement of the scissor blades 14 and 16 towards each other or away from each other remains possible.

From FIG. 3 it is evident that the two scissor blades 14 and 16 are slightly curved. It is also shown that the scissor blade 16 on its side pointing in the direction towards the scissor blade 14 is provided with an electrically insulating ceramic layer 90 which forms a functional component. In a similar way, the scissor blade 14 is provided with a ceramic layer 92 pointing in the direction towards the scissor blade 16.

Each of FIGS. 4 to 8 shows that the scissor blade 14 in the form of a metallic carrier 94 is adhesively bonded to the ceramic layer 92. To insulate the two scissor blades 14 and 16 from each other, the ceramic layer 92 is constructed in the area of the bearing pin 18 as a bearing bush 96, so that a short circuit cannot occur between the carrier 94 of the scissor blade 14 and a metallic carrier 98 of the scissor blade 16.

FIG. 5 shows the special construction of the scissor blade 14 in cross section. Only in the area of a cutting edge 100 do the carrier 94 and the ceramic layer 92 bear directly on each other and hence without any gap therebetween. There is therefore no gap between contact surfaces 102 of the carrier and 104 of the ceramic layer bearing on each other, and so no adhesive can get in between these two layers.

The further surface of the carrier 94 pointing towards the ceramic layer 92 and not serving as contact surface 102 forms an adhesive surface 106, the further surface of the ceramic layer 92 an adhesive surface 108. The adhesive surface 106 of the carrier 94 comprises a flat adhesive groove 110 in which an adhesive projection 112 of the ceramic layer 92 engages, but does not fill this out in a positively locking manner. There is thus formed between the carrier 94 and the ceramic layer 92 an adhesive gap 114 which also surrounds the adhesive projection 112.

A suitable adhesive is introduced into the adhesive gap 114 to bond the carrier 94 to the ceramic layer 92.

To prevent tilting of the ceramic layer 92 relative to the carrier 94 about an edge 118 of the carrier 94, which delimits the contact surface 102 towards the adhesive gap 114, additional spacers 120 in the form of small, elongated, parallelepipedal members having a height which corresponds to the width of the adhesive gap 114 are arranged at regular spacings on the adhesive projection 112 or on one of the adhesive surfaces 106 or 108. End faces 122 of the spacers 120 then lie directly against the adhesive surface 106 of the carrier 94 without any gap therebetween.

Alternative embodiments of spacers are shown in FIGS. 7 and 8. In FIG. 7, spacers 124 in the form of small pyramids are integrally formed on the ceramic layer, with apexes of the spacers 124 touching the adhesive surface 106 of the carrier 94 in the form of dots. In this way, with the desired spacing being maintained between the two adhesive surfaces 106 and 108, the adhesive surface 106 of the carrier 94, which is covered with adhesive 116, can be maximized.

A third variant of a possible spacer is shown in FIG. 8. To maintain the spacing between the adhesive surface 106 of the carrier 94 and the adhesive surface 108 of the ceramic layer 92, a plurality of balls 126 are mixed with the adhesive 116, with the diameter of the balls 116 being selected so as to correspond to the desired width of the adhesive gap 114. Owing to their shape, the balls 126 distribute themselves more or less uniformly between the adhesive surfaces 106 and 108.

Furthermore, the adhesive surface 106 and likewise the adhesive surface 108 may, in addition, be structured or microstructured in an optional manner in order to enlarge the surface wetted and covered with adhesive 116. This is indicated in the cross section in FIG. 5, by way of example, by formation of the adhesive groove 110 and the adhesive projection 112.

FIG. 9 shows a cross-sectional view of a fourth variant of a scissor blade, as described in conjunction with FIGS. 1 to 5. Elements of the scissor blades which are identical or of very similar construction are, therefore, designated by identical reference numerals with the addition of the suffix "a".

A major difference from the embodiment described in conjunction with FIG. 5 is that, strictly speaking, the two contact surfaces 102a and 104a do not form contacting surfaces, but contacting lines. In this way, as a whole, a common contacting line 103a is formed, which closes the adhesive gap 114a, which tapers in the shape of a wedge in the direction towards the contacting line 103a, in the area of the cutting edge 100a. Consequently, when an instrument constructed with the above-described scissor blade is used, a current flowing along a coagulation path 128a along the cutting edge 100a will not come into contact with the adhesive 116a introduced into the adhesive gap 114a between the adhesive surfaces 106a and 108a and bring about evaporation thereof. The two contact surfaces 104a and 102a are inclined at an angle of inclination 130a relative to each other, which has a value of approximately 10°.

A fifth embodiment of a scissor blade according to the invention is shown in cross section in FIG. 10. As in the embodiment shown in FIG. 9, identical elements or elements similar to those of the embodiment described in conjunction with FIGS. 1 to 5 are designated by identical reference numerals with the addition of the suffix "b".

The fifth embodiment corresponds in its basic design to the fourth embodiment, but differs in that the contact surfaces 102b and 104b are each in the form of two plane surface portions, which results in a surface-to-surface contacting of the two contact surfaces 102b and 104b starting from the cutting edge 100b. The contact surface 102b is of completely plane design. The contact surface 104b has two surface sections which are inclined relative to each other, with the one surface section extending parallel to the contact surface 102b and resting thereon, and the other surface section extending through an angle of inclination 130b at an incline to the contact surface 102b, so that here, too, a wedge-shaped adhesive gap can form between the inclined surface sections of the contact surfaces 102b and 104b. In the present embodiment, the angle of inclination 130b has a value of approximately 10°. Owing to the surface-to-surface contacting of the contact surfaces 102b and 104b bearing on each other, a coagulation path 128b along the cutting edge 100b is even further away from the adhesive 116b joining the carrier 94b to the ceramic layer 92b, so that evaporation thereof is virtually impossible.

The two construction variants, as described in FIGS. 9 and 10, may also be provided with spacers, as explained in further detail in conjunction with FIGS. 6 to 8.

The invention claimed is:

1. Surgical instrument with at least one tool, said tool comprising:
   a carrier, and
   at least one functional component,
   wherein:
      the carrier comprises a first contact surface,
      the functional component comprises a second contact surface,
      the at least one functional component is adhesively bonded to the carrier,
      the carrier and the functional component are manufactured as two separate parts,
      the first contact surface bears directly and without adhesive on the second contact surface with no gap therebetween,
      the carrier has a first adhesive surface, the functional component has a second adhesive surface,
      the first adhesive surface is separated from the second adhesive surface by an adhesive gap,
      the adhesive gap is filled with an adhesive layer which is substantially formed by an adhesive, and
      the adhesive gap is of wedge-shaped construction at least section-wise.

2. Instrument in accordance with claim 1, wherein the at least one tool is a scissor blade comprising a cutter with a cutting edge, and the first and second contact surfaces bear in an area of the cutting edge directly on each other or pass into the cutting edge.

3. Instrument in accordance with claim 1, wherein the first contact surface and the second contact surface bear on each other along at least one contacting line with no gap therebetween.

4. Instrument in accordance with claim 1, wherein the first contact surface and the second contact surface bear surface-to-surface on each other at least section-wise in an area of a common contacting surface with no gap therebetween.

5. Instrument in accordance with claim 1, wherein a thickness of the wedge-shaped adhesive gap decreases in a direction towards the first and second contact surfaces bearing on each other.

6. Instrument in accordance with claim 1, wherein at least one spacer is arranged in the adhesive gap between the first and second adhesive surfaces.

7. Instrument in accordance with claim 6, wherein at least one of the first adhesive surface and the second adhesive surface carries the at least one spacer.

8. Instrument in accordance with claim 6, wherein the adhesive contains the at least one spacer.

9. Instrument in accordance with claim 6, wherein a plurality of spacers are provided.

10. Instrument in accordance with claim 6, wherein the at least one spacer is one of a spherical, pyramidal, conical, cylindrical or parallelepipedal shape.

11. Instrument in accordance with claim 1, wherein a surface of at least one adhesive surface comprises at least one structured surface portion.

12. Instrument in accordance with claim 11, wherein the structured surface portion essentially has a symmetrical structure.

13. Instrument in accordance with claim 11, wherein the structured surface portion is microstructured.

14. Instrument in accordance with claim 1, wherein a surface of at least one of the first adhesive surface and the second adhesive surface is larger than a projection of at least one of the first adhesive surface and the second adhesive surface in a direction towards the respective other adhesive surface.

15. Instrument in accordance with claim 1, wherein the carrier is electrically conductive and the functional component is electrically non-conductive.

16. Instrument in accordance with claim 15, wherein the electrically non-conductive functional component is made of a ceramic material, and the electrically conductive carrier is made of a metal.

17. Instrument in accordance with claim 1, wherein:
the at least one tool comprises at least a first tool and a second tool, and
the first tool is movable relative to the second tool.

18. Instrument in accordance with claim 17, wherein the first tool is mounted for pivotal movement relative to the second tool.

19. Instrument in accordance with claim 1, wherein the instrument is a tubular shaft instrument with an elongated shaft, and the at least one tool is movably mounted at a distal end of the shaft.

20. Instrument in accordance with claim 1, wherein the instrument is scissors.

21. Surgical instrument with at least one tool, said tool comprising:
a carrier, and
at least one functional component,
wherein:
the carrier comprises a first contact surface,
the functional component comprises a second contact surface,
the at least one functional component is adhesively bonded to the carrier,
the carrier and the functional component are manufactured as two separate parts,
the first contact surface bears directly and without adhesive on the second contact surface with no gap therebetween,
the first contact surface defines at least section-wise a first plane,
the second contact surface defines at least section-wise a second plane, and
the first plane and the second plane are inclined at an angle of inclination relative to each other and intersect in a contacting line of the first and second contact surfaces.

22. Instrument in accordance with claim 21, wherein the angle of inclination is less than 45°.

23. Surgical instrument with at least one tool, said tool comprising:
a carrier, and
at least one functional component,
wherein:
the carrier comprises a first contact surface and a first adhesive surface,
the functional component comprises a second contact surface and a second adhesive surface,
the at least one functional component is adhesively bonded to the carrier with an adhesive,
the first contact surface bears on the second contact surface with no gap therebetween,
the first adhesive surface is separated from the second adhesive surface by an adhesive gap which is of wedge-shaped construction at least section-wise, and
the adhesive gap is filled with an adhesive layer which is substantially formed by the adhesive.

24. Instrument in accordance with claim 23, wherein a thickness of the wedge-shaped adhesive gap decreases in a direction towards the first and second contact surfaces bearing on each other.

25. Instrument in accordance with claim 23, wherein the first contact surface defines at least section-wise a first plane, the second contact surface defines at least section-wise a second plane, and the first plane are inclined at an angle of inclination relative to each other and intersect in a contacting line of the first and second contact surfaces.

26. Instrument in accordance with claim 25, wherein the angle of inclination is less than 45°.

27. Instrument in accordance with claim 23, wherein the first contact surface bears at least one of directly and without adhesive on the second contact surface.

* * * * *

UNITED STATES PATENT AND TRADEMARK OFFICE
CERTIFICATE OF CORRECTION

PATENT NO. : 7,422,590 B2 Page 1 of 1
APPLICATION NO. : 10/848543
DATED : September 9, 2008
INVENTOR(S) : Kupferschmid et al.

It is certified that error appears in the above-identified patent and that said Letters Patent is hereby corrected as shown below:

Column 10, line 34 is corrected to read: --second plane, and the first plane and the second plane are inclined at an angle of--

Signed and Sealed this

Fourth Day of November, 2008

JON W. DUDAS
*Director of the United States Patent and Trademark Office*